United States Patent
Viker (10) Patent No.: US 10,383,717 B2
(45) Date of Patent: Aug. 20, 2019

(54) IMPLANTS, TOOLS, AND METHODS FOR TREATMENTS OF PELVIC CONDITIONS

(71) Applicant: Boston Scientific Scimed, Inc., Maple Grove, MN (US)

(72) Inventor: Thomas O. Viker, Arden Hills, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 268 days.

(21) Appl. No.: 14/775,203

(22) PCT Filed: Mar. 3, 2014

(86) PCT No.: PCT/US2014/019871
§ 371 (c)(1),
(2) Date: Sep. 11, 2015

(87) PCT Pub. No.: WO2014/149612
PCT Pub. Date: Sep. 25, 2014

(65) Prior Publication Data
US 2016/0022404 A1   Jan. 28, 2016

Related U.S. Application Data

(60) Provisional application No. 61/789,221, filed on Mar. 15, 2013.

(51) Int. Cl.
*A61F 2/00* (2006.01)
*D03D 1/00* (2006.01)
(Continued)

(52) U.S. Cl.
CPC .......... *A61F 2/0063* (2013.01); *A61F 2/0045* (2013.01); *D03D 1/00* (2013.01);
(Continued)

(58) Field of Classification Search
CPC .................. A61F 2/0045; A61F 2/0063; A61F 2250/0015; A61F 2250/0018; A61F 2250/0068
See application file for complete search history.

(56) References Cited

U.S. PATENT DOCUMENTS 6,884,212 B2  4/2005  Thierfelder et al.
2005/0043818 A1  2/2005  Bellon Caneiro et al.
(Continued)

FOREIGN PATENT DOCUMENTS

WO   2010087923 A1   8/2010
WO   2014008130 A1   1/2014

OTHER PUBLICATIONS

Extended European Search Report for European Application No. 14771142.8, dated Sep. 21, 2016, 8 pages.

*Primary Examiner* — Thaddeus B Cox
(74) *Attorney, Agent, or Firm* — Brake Hughes Bellermann LLP (57) ABSTRACT

Described are implants, intermediate articles of manufacture (web constructions) useful for preparing implants, methods of forming the implants and intermediate articles, and related methods for treating pelvic conditions by use of the implants. The present invention relates generally to surgical implants (i.e., "implants"), intermediate articles of manufacture (web constructions) useful for preparing surgical implants, methods of forming the implants and intermediate articles, and related methods for treating pelvic conditions by use of the implants.

9 Claims, 5 Drawing Sheets (51) Int. Cl.
 *D03D 3/00* (2006.01)
 *D04B 1/22* (2006.01)
 *D03D 11/02* (2006.01)
 *D03D 15/08* (2006.01)

(52) U.S. Cl.
 CPC ............... *D03D 3/00* (2013.01); *D03D 3/005* (2013.01); *D03D 11/02* (2013.01); *D03D 15/08* (2013.01); *D04B 1/22* (2013.01); *A61F 2002/0068* (2013.01); *A61F 2220/0075* (2013.01); *A61F 2240/001* (2013.01); *A61F 2250/0015* (2013.01); *A61F 2250/0018* (2013.01); *D10B 2509/08* (2013.01)

(56) References Cited

U.S. PATENT DOCUMENTS

| | | | |
|---|---|---|---|
| 2010/0081865 A1* | 4/2010 | Hamati | A61F 2/0045 600/37 |
| 2011/0297161 A1 | 12/2011 | Deitch | |
| 2012/0022318 A1 | 1/2012 | Thierfelder et al. | |
| 2012/0108894 A1 | 5/2012 | Young et al. | |
| 2013/0066146 A1* | 3/2013 | Olivieri | A61F 2/0045 600/37 |
| 2014/0005471 A1* | 1/2014 | Amarasinghe | A61F 2/0004 600/37 |

\* cited by examiner

IMPLANTS, TOOLS, AND METHODS FOR TREATMENTS OF PELVIC CONDITIONS

PRIORITY CLAIM

The present application claims the benefit from International Application No. PCT/US2014/019871, filed Mar. 3, 2014, which in turn claims priority under 35 USC § 119(e) from U.S. Provisional Patent Application having Ser. No. 61/789,221, filed on Mar. 15, 2013, titled IMPLANTS, TOOLS, AND METHODS FOR TREATMENTS OF PELVIC CONDITIONS, the disclosures of which are incorporated herein by reference in their entireties.

FIELD OF THE INVENTION

The present invention relates generally to surgical implants (i.e., "implants"), intermediate articles of manufacture (web constructions) useful for preparing surgical implants, methods of forming the implants and intermediate articles, and related methods for treating pelvic conditions by use of the implants.

BACKGROUND

Pelvic health for men and women is a medical area of increasing importance, at least in part due to an aging population. Examples of common pelvic ailments include incontinence (e.g., urinary or fecal), pelvic tissue prolapse (e.g., female vaginal prolapse), and conditions of the pelvic floor. Urinary incontinence can further be classified as including different types, such as stress urinary incontinence (SUI), urge urinary incontinence, mixed urinary incontinence, among others. Other pelvic floor disorders include cystocele, rectocele, enterocele, and prolapse such as anal, uterine and vaginal vault prolapse. Pelvic disorders such as these can result from weakness or damage to normal pelvic support systems.

In its severest forms, vaginal vault prolapse can result in the distension of the vaginal apex outside of the vagina, and is often associated with a rectocele, cystocele or enterocele. An enterocele is a vaginal hernia in which the peritoneal sac containing a portion of the small bowel extends into the rectovaginal space. Vaginal vault prolapse and enterocele represent challenging forms of pelvic disorders for surgeons. One known method of repairing vaginal vault prolapse is by suturing to the supraspinous ligament or attaching the vaginal vault through mesh or fascia to the sacrum. Many patients suffering from vaginal vault prolapse also require a surgical procedure to correct stress urinary incontinence that is either symptomatic or latent. Many of these procedures often involve lengthy surgical procedure times.

There is continuous interest in providing new and advantageous implants and related methods for use in treating pelvic conditions such as vaginal prolapse. It is also desirable that such implants can be manufactured by efficient and cost effective manufacturing processes.

SUMMARY

Implantable devices, methods of their preparation and use, related intermediate articles (web constructions), systems, and methods as described can be used to prepare devices, articles, and systems useful to treat pelvic conditions such as vaginal prolapse, including various forms such as enterocele, cystocele, rectocele, apical or vault prolapse, uterine descent, etc. Implants as described can also be useful for treating other pelvic conditions such as incontinence, levator conditions, levator defects, and other conditions caused by muscle and ligament weakness, hysterectomies and the like. While many of the surgical procedures and devices described herein are directed to transvaginal or laparoscopic surgical procedures in a female patient, it is understood that the implants can also be surgically placed in a male or female patient by alternate techniques and for treating different conditions.

One procedure that can be used to treat vaginal prolapse conditions is sacral colpopexy. A sacral colpopexy procedure involves placing an implant (e.g., a Y-sling) between tissue to be supported (e.g., tissue of a vaginal vault) and supportive tissue (e.g., tissue at a posterior pelvic region such as at a region of sacral anatomy), to secure the implant to supportive tissue and the supported tissue, to provide therapeutic support for the supported tissue. Implants for these procedures are known, as described and illustrated at Assignee's co-pending provisional patent application having U.S. Ser. No. 60/583,146, filed Jun. 25, 2004, the entirety of which is incorporated herein by reference.

Previous to the present description, many methods for preparing these implants (e.g., Y-slings), which include multiple layers of implant material at a portion of the implant, have involved non-continuous steps of cutting implant material and then bonding one implant material to another implant material to produce a multi-layer portion of the implant.

The present description explains new methods of continuously or otherwise efficiently forming implants that include a portion that has two adjacent layers or leafs, such as but not limited to a "Y-mesh" or "Y-sling" implant. The adjacent layers or leafs are held together at a junction that allows the two layers to contact each other at opposing major surfaces of the two layers. The two layers, being of implant material that can be relatively flexible and pliable, can also be separated to allow the surfaces to be held apart, such as to surround tissue to be supported, e.g., vaginal vault tissue. The implant also optionally and preferably includes an additional portion that connects to the multi-layer portion, the additional portion having, e.g., a single layer or multiple layers. The different layers or portions may be made of implant material that is useful as an implant material; each layer or portion of an implant may exhibit physical properties that are the same or different from physical properties of a different layer or portion of the same implant. The referenced physical properties include flexibility, elasticity, weave or knit or fenestration pattern, coloration, density, length, width, and the like.

Also described are certain web materials and web constructions that are useful as intermediate structures in preparing the implants. The web materials are in the form of web constructions that include different segments of open pore implant materials, each segment being a precursor to a segment of an implant, the implant being formed upon cutting the different segments. A web construction may include a series of repeating segments that includes one repeating segment constructed of multiple (two) separate open pore implant material layers joined at ends of the segment by a junction or another different segment. The series of repeating segments may also include one repeating segment of a combined open pore implant material that is made by inter-weaving (e.g., inter-twining) layers of open pore implant material; the inter-woven material can be a single layer of open pore material constructed from two layers of open pore implant material that make up an adjacent segment as separate layers. The different segments, single (inter-woven) or multiple open pore implant materials, and optional junctions, can be continuously provided or continuously formed and are joined or inter-woven intermittently, at regular and pre-determined intervals, to produce lengths of adjacent segments that embody multiple implants. The web construction can be cut at multiple calculated periodic (regular) length-wise locations in a width-wise direction to produce a series of implants.

In one aspect, the invention relates to an implant. The implant includes: a base having a length of continuous open pore implant material between a first end and a second end; a sacral leaf at the first end and a first vaginal leaf at the second end; and a second vaginal leaf having an attached end and a loose end, the attached end being attached to the base along a width of the base. The first vaginal leaf has implant material having a first vaginal leaf elasticity, a first vaginal leaf width, a first vaginal leaf fenestration pattern, and a first vaginal leaf density. The second vaginal leaf has implant material having a second vaginal leaf elasticity, a second vaginal leaf width, a second vaginal leaf fenestration pattern, and a second vaginal leaf density. The sacral leaf has implant material having a sacral leaf elasticity, a sacral leaf width, a sacral leaf fenestration pattern, and a sacral leaf density. One or more of the following conditions is met: the sacral leaf elasticity is different from the first vaginal leaf elasticity, the sacral leaf elasticity is different from the second vaginal leaf elasticity, the sacral leaf width is different from the first vaginal leaf width, the sacral leaf width is different from the second vaginal leaf width, the sacral leaf density is different from the first vaginal leaf density, the sacral leaf density is different from the second vaginal leaf density, the sacral leaf fenestration pattern is different from the first vaginal leaf fenestration pattern, or the sacral leaf fenestration pattern is different from the second vaginal leaf fenestration pattern.

In another aspect, the invention relates to a longitudinal web having a length of upper implant material and a length of lower implant material. The longitudinal web includes: a first vaginal leaf segment along which a segment of the length of upper implant material is separated from a segment of the length of lower implant material; a first sacral leaf segment adjacent to the first vaginal leaf segment; a second vaginal leaf segment adjacent to the first sacral leaf segment, along which a segment of the length of upper implant material is separated from a segment of the length of lower implant material; and a second sacral leaf segment adjacent to the second vaginal leaf segment.

Another aspect of the invention relates to a method of preparing a two-layer implant material web. The method includes: providing a length of upper implant material; providing a length of lower implant material; forming a first junction to join the upper implant material and the lower implant material at a first junction location; forming a second junction to join the upper implant material and the lower implant material at a second location spaced a lengthwise distance from the first junction location to form a first segment comprising a length of upper implant material separated from a length of lower implant material between the first junction and the second junction, and forming a third junction to join the upper implant material and the lower implant material at a third location spaced a lengthwise distance from the second junction location, to form a second segment comprising a length of upper implant material separated from a length of lower implant material between the second junction and the third junction.

In another aspect, the invention relates to a method of continuously preparing an open pore implant material web. The method includes: providing upper implant material; providing lower implant material; forming a first segment comprising a length of the upper implant material and a separate length of the lower implant material; forming a second segment adjacent to the first segment, the second segment comprising a length of combined implant material comprising upper implant material interwoven with lower implant material; forming a third segment adjacent to the second segment, the third segment comprising a length of the upper implant material and a separate length of the lower implant material; and forming a fourth segment adjacent to the third segment, the fourth segment comprising a length of combined implant material comprising upper implant material interwoven with lower implant material.

BRIEF DESCRIPTION OF THE DRAWINGS

All figures are schematic and are not to scale.

DETAILED DESCRIPTION

The present description relates to implants, methods of making implants, and methods of using implants. The description also relates to certain web materials and web constructions that are useful as intermediate structures in preparing the implants. The web materials are in the form of elongate, segmented, web constructions; a segment may be made either two separate layers of (upper and lower) implant materials, or a single layer of a combined implant material; segments may optionally be joined at multiple junctions placed at periodic locations along the length of the web. The layers and multiple optional junctions can be continuously provided or continuously formed and are joined at the junctions or at the combined implant material segments, to produce lengths of repeating segments that embody multiple implants. The web construction can be cut at multiple calculated periodic length-wise locations, in a width-wise direction, to produce a multiple implants.

Implants as described may be of a type that is useful as a surgical implant to support tissue in a method of addressing and treating a condition of pelvic tissue, such as to address a pelvic floor disorder such as prolapse (e.g. vaginal, such as vaginal vault prolapse), enterocele (e.g. of the uterus), rectocele, and cystocele. Non-urological procedures such as eventration or hernia repair, and visceral, parietal, and neurological procedures, are also applications for an implant as described. In a preferred embodiment, an implant as described is used in a sacral colpopexy procedure. It is contemplated that the implant may also be useful in conjunction with other procedures such as but not limited to culposuspension, culdoplasty, procedures for addressing cystocele prolapse, and other surgical procedures that use an implant. Examples of implants that include features in common with implants of the present description are shown and described in Assignee's co-pending application having U.S. Publication No. 2012/0022318, filed Oct. 4, 2011, by Thierfelder et al., entitled IMPLANTABLE ARTICLE AND METHOD, the entirety of which is incorporated herein by reference.

The dimensions, size, and shape of an implant can be a function of the placement of the implant and therapeutic treatment for which the implant is used. Exemplary implants can include those that have multiple (at least two) discernible portions, with least one portion having a single layer and at least one portion having a set of two layers (or "leafs"). The portion that includes the set of at least two opposing leafs or layers will include an arrangement of the two leafs or layers that places the layers adjacent to one another with major surfaces of each layer in contact. The two leafs are connected at a junction, and a third layer or leaf extends from one of the two opposing leafs or layers, also optionally from the junction, that is integrally connected with and formed with one of the two opposing leafs or layers.

The assembled implant can have dimensions and physical and mechanical properties useful to a suited purpose, such as a suited therapeutic application, e.g., for use in a sacrocolpopexy procedure, or for a different pelvic tissue treatment. To provide a suited set of mechanical and physical properties for a particular implant, each leaf or layer of an implant may independently have the same or different mechanical or physical properties, even if integrally connected, integrally formed, or both. These physical and mechanical properties include but are not limited to: weave or knit pattern, fenestration pattern, implant material density, implant material elasticity, stiffness, color. For example, one portion, leaf, or layer of an implant may exhibit a higher implant material density compared to a different portion, leaf, or layer of the same implant; one portion, leaf, or layer of an implant may exhibit greater elasticity or greater stiffness compared to a different portion, leaf, or layer of the same implant; one portion, leaf, or layer of an implant may exhibit a different color or color pattern compared to a different portion, leaf, or layer of the same implant; one portion, leaf, or layer of an implant may exhibit a different weave, knit, or fenestration pattern compared to a different portion, leaf, or layer of the same implant. Different portions, leafs, or layers may also have different dimensions.

The material used to prepare the implant and portions (e.g., layers or leafs) thereof, which can be any suitable "implant material," can be a known material that is suitable for use as an implant, such as a continuously produced, woven, knitted, extruded, or other open pore material made from connected strands, fibers, threads, filament (e.g., monofilament), treated film, or the like, which may be natural or synthetic. Exemplary implant materials include woven, non-woven (but still fibrous or filamentary), knitted, or other materials having inter-linked filaments or fibers that form multiple fiber junctions and multiple regular or randomly sized and spaced apertures. Implant embodiments that use monofilament fibers or multi-filament fibers are useful, as are embodiments that include two or more types of different (monofilament, multi-filament, or a combination) fibers used to produce an implant material. Fiber junctions may be formed via weaving, bonding (e.g., adhesive bonding, thermo-bonding, etc.), tying, ultrasonic welding, knitting, or other junction-forming techniques, including combinations thereof. The size of the resultant openings, pores, apertures, or fenestrations, etc., is sufficient to allow tissue in-growth and fixation of the open pore implant material within surrounding tissue, after the implant is placed at an anatomical location such as a pelvic region. As an example, not intended to be limiting, apertures of an open pore material may take a form of elliptical, square, circular, rectangular, or diamond shaped apertures having a diagonal or diameter dimension in a range of about 0.040 inches (1.016 mm) to about 0.055 inches (1.397 mm). Preferred such open pore implant materials may be continuously produced or assembled into the open-pore implantable material for use as described herein for manufacturing to continuously formed a useful implant such as the described Y-mesh implant.

Strands, layers, or filaments, etc., of an open pore implant material can be of any material useful to form a surgical implant. Suitable natural and polymeric materials are biocompatible, optionally bioabsorbable, and may be coated to encourage tissue ingrowth or prevent infection. Examples include nylon, polyethylene terephthalate, polyolefins such as polypropylene and polyethylene, poly-L-lactide (PLLA), polyethylene glycol (PGA), polyester, and any combination of materials. Depending on the desired treatment, the polymer may be absorbable, non-absorbable, or resorbable. Commercial examples of useful polymers are available under the trade names Prolene™ and Deklene™. Another example is Marlex™ material. Yet another example, not intended to be limiting, is woven polypropylene monofilament, knitted with a warp tricot.

An implant or portions or fiber thereof may have one or more features or substances associated therewith, presented by a process such as coating or interweaving. Examples of features and substances include, without limitation, drugs, hormones, antibiotics, coloration or demarcation, antimicrobial substances, dyes, silicone elastomers, acetal, polyurethanes, radiopaque filaments or substances, anti-bacterial substances, chemicals or agents, or any combinations of two or more of these. The substances may be used to enhance a treatment effect, reduce the potential for implant erosion or rejection by the body, enhance visualization, indicate proper sling orientation, resist infection, promote healing, increase softness, improve another mechanical property (e.g., stiffness), or to provide another desirable effect or property in an implant.

Figure 1A:
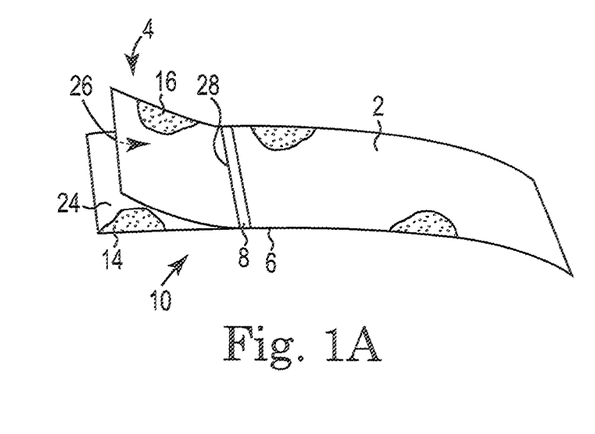
FIGS. 1A, 1B, and 1C show an embodiment of an implant.
Figure 1B:
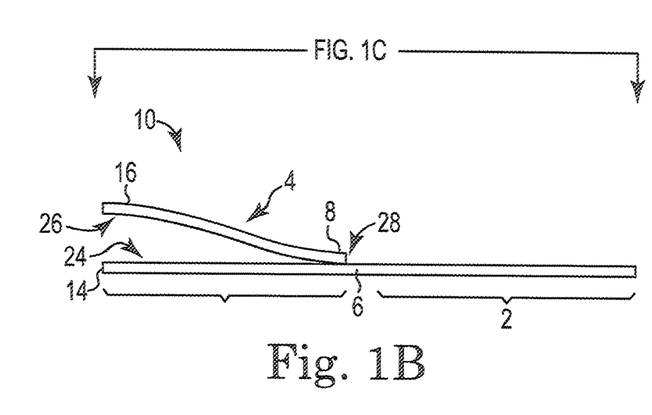
Figure 1C:
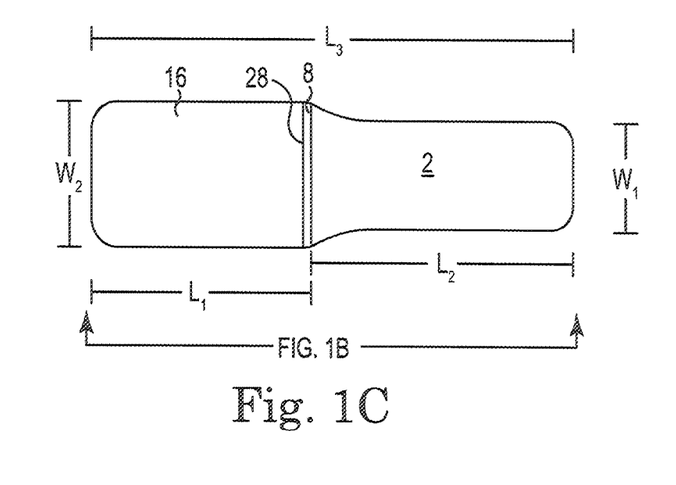

FIGS. 1A, 1B, and 1C (side perspective view, side view, and top view, respectively) illustrate one example of an implant, which can be referred to as a "Y-mesh," and that can be prepared and useful according to the present description. The Y-mesh is a style of implant that includes multiple identifiable portions, at least one portion having a single layer and another portion having two layers, e.g., an end portion (2) having a single layer and a head portion (4) having multiple layers. Each layer and portion is made of implant material. Exemplary Y-mesh implants may be useful for supporting vaginal tissue in a sacrocolpopexy procedure, but other uses with alternate therapeutic methods of treatments, for similar Y-mesh or for other multi-layer implants, are also understood.

Referring to FIGS. 1A, 1B, and 1C, head portion 4 of implant 10 includes two separate pieces or layers (14, 16) of implant material, with adjacent major surfaces (24, 26) that face and are opposed to one another and are capable of contacting each other. A single piece of continuous implant material, base 6, extends in a length-wise direction between the ends of implant 10, with the length (L3) of base 6 (also the total length L3 of implant 10) equal to the length (L2) of end portion 2 and the length (L1) of one layer (14) of head portion 4. The second layer (16) of head portion 4 includes a joined edge or end 28 that is bonded to, connected to, interwoven with, or otherwise secured to base 6 at junction 8 in a width-wise direction and at a length-wise location between opposing ends of base 6; junction 8 can be generally at a location that can be considered to divide end portion 2 from layer 14 of head portion 4. Junction 8 can be considered to constitute a three-way joint, connection, or branch, at which ends of the two leafs or layers (14, 16) of head portion 4 meet and connect to each other, and meet and connect to an end of end portion 2. Width W1 of end portion 2 can be the same or different compared to width W2 of head portion 4; as illustrated, width W1 is less than width W2.

Junction 8, which secures end 28 of layer (vaginal leaf) 14 to base 6, can be any suitable junction structure that will secure end 28 to base 6, across a width of each piece, to securely hold layer 14 to base 6 during use of implant 10. Examples of suitable junctions can be a heat-bond, a weld, an adhesive junction, an interwoven or knit or otherwise tied or intertwined connection of strands from layer 14 with strands of base 6, or a suture connection (i.e., a connection made using a suture structure that is separate from strands, filaments, etc., of layer 14 or base 6). Examples of adhesives include tissue adhesives, tissue sealants, biocompatible bonding agents (e.g. silicone), and biocompatible adhesives. Examples of heat and weld bonds include radio frequency (RF) and ultrasonic welding, and heating to melt polymeric material of layer 14 and base 6 together.

Implant 10 of FIGS. 1A, 1B, and 1C is a single non-limiting example of an implant (i.e., a "Y-mesh"), and is useful in particular for supporting posterior vaginal tissue in a sacrocolpopexy procedure. Referring to FIGS. 1A, 1B, and 1C, implant 10 useful in a sacral colpopexy procedure is illustrated to include end portion (sacral leaf) 2 and head portion 4 that includes first tissue engagement layer (first vaginal leaf or first layer) 14 and second tissue engagement layer (second vaginal leaf or second layer) 16. Each of the tissue engagement layers 14 and 16 extends from end portion 2, with tissue engagement layer 14 being integral to end portion 2 and tissue engagement layer 16 being separate but connected at junction 8. Base 6 is a continuous piece of implant material integrally forming first vaginal leaf 14 and sacral leaf 2; edge 28 of the second vaginal leaf 16 meets base portion 6 at junction 8. Junction 8 extends in a width-wise direction approximately at the integrally connected boundary between first vaginal leaf 14 and sacral leaf 2.

Figure 2:
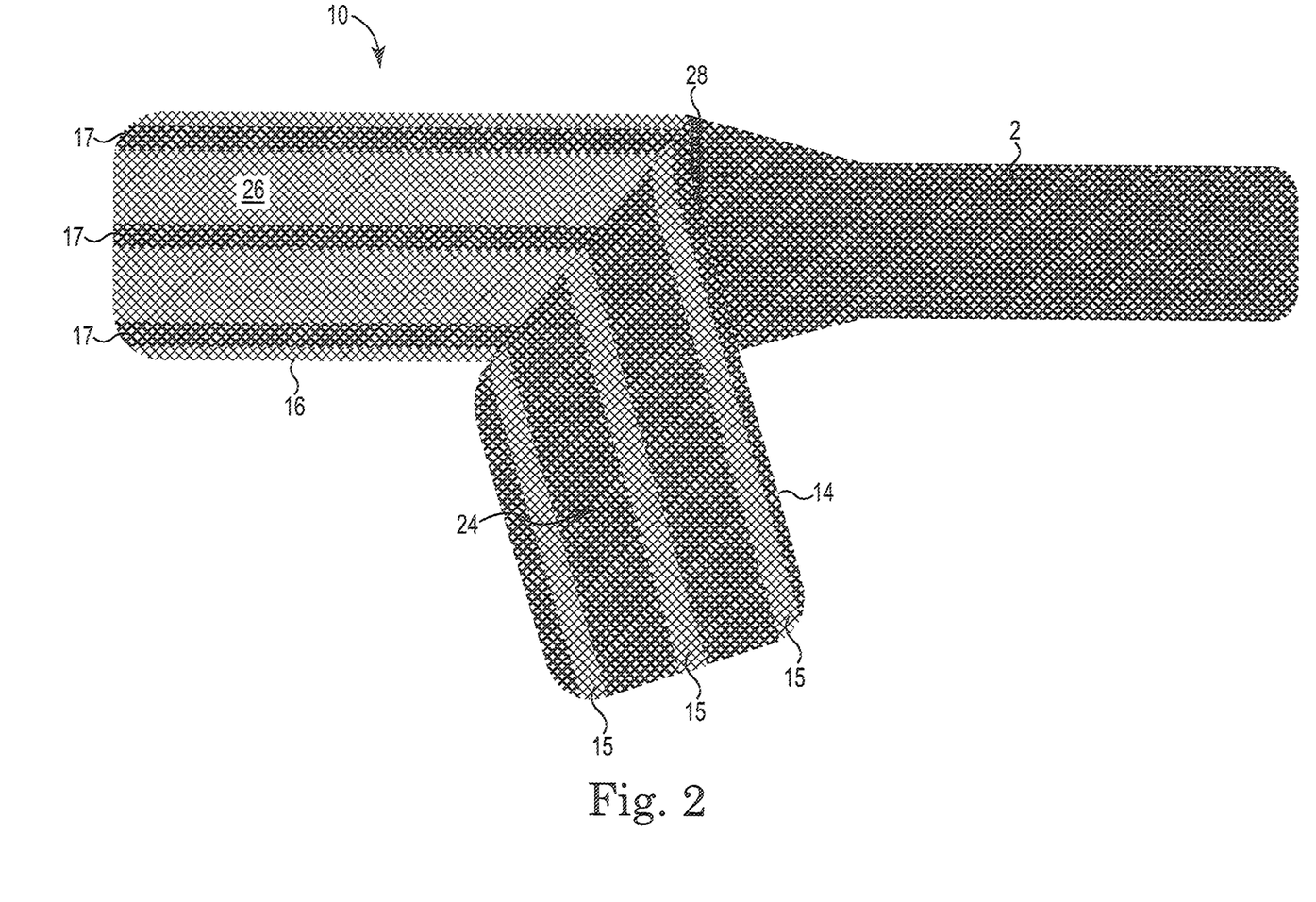
FIG. 2 shows an embodiment of an implant.

Referring to FIG. 2, illustrated (top view) is another embodiment of a Y-mesh that is prepared and has a structure according to this description. Implant 10 is similar to that of FIGS. 1A, 1B, and 1C, including the overall structure and the structure of end portion (sacral leaf) 2 and vaginal leafs 14 and 16, all of an implant material such as a knit open pore mesh. (As illustrated, vaginal leaf 14 is shown to be folded away from vaginal leaf 16, and pulled laterally to allow a portion of surface 24 of vaginal leaf 14 to be shown in the illustration.) Additional features of the embodiment of FIG. 2 include a color of sacral leaf 2 (e.g., blue), and color to each of vaginal leafs 14 (blue with white longitudinal stripes 15) and 16 (white with blue longitudinal stripes 17). According to certain embodiments, vaginal leaf 14 can have coloration that is different from the coloration of vaginal leaf 16 (e.g., blue). That way, a surgeon can plan for placement of each coloration at anterior and a posterior vaginal tissue prior to surgery to ensure that the correct leaf is attached to the correct location (posterior or anterior) of the vaginal tissue, and to avoid the possibility of placing and securing an incorrect surface of a leaf the tissue (to avoid the possibility of placing an "outside" surface of a vaginal leaf to the tissue). Still another feature of the embodiment of FIG. 2 is the presence of longitudinal demarcations, lines 17 and 15, at vaginal leafs 16 and 14, respectively. These lines facilitate placement on vaginal tissue of a patient by identifying a centerline and lateral locations in a length-wise direction along the lengths of the two vaginal leafs 14 and 16. Some or all end corners of sacral and vaginal leafs 2, 14, and 16 are rounded, and the width of sacral leaf 2 is less than the width of vaginal leafs 14 and 16. Lengths of leafs 2, 14, and 16 are approximately equal, e.g., from 10 to 12 centimeters each.

According to certain implant embodiments, different portions or regions of an implant may exhibit similar or dissimilar dimensions and physical and mechanical properties. As a first example, each of sacral leaf 2, vaginal leaf 14, and vaginal leaf 16, exhibits properties of: density, elasticity, stiffness, knit or weave or fenestration pattern, length, width, and thickness. According to various embodiments of implants, these properties of the three leafs (2, 14, and 16) of a single implant may be the same or different.

One property of an implant material, implant, or portion (e.g., leaf) of an implant, is elasticity, especially in a longitudinal direction. According to embodiments of implants, a vaginal leaf (e.g., two vaginal leafs) can exhibit an elasticity that is different from an elasticity of a sacral leaf A vaginal leaf attaches to vaginal tissue and can desirably conform to vaginal tissue after implantation; a sacral leaf supports the two vaginal leafs and vaginal tissue secured thereto by attachment to supportive tissue and can desirably support the vaginal tissue without undue movement. Accordingly, the vaginal leafs may suitably exhibit a certain level of elasticity (meaning elasticity in the length-wise direction) that is greater than the elasticity (again in the length-wise direction) of the sacral leaf; the elasticity of the sacral leaf can be suitably low to prevent undue extension of the sacral leaf after therapeutic placement between the vaginal tissue and supportive tissue, to prevent undue movement of the vaginal tissue after therapeutic placement and attachment of the implant.

Elasticity (also sometimes referred to as "elongation") is a known mechanical property of implant materials and can be measured by standard measurements. As an example, elasticity may be measured using a commercially available Instron™ device. Elasticity of an implantable material can be affected by both the composition of implant material used to prepare the implant (e.g., chemical composition and mechanical properties of strands or filaments of a fenestrated film), and the structure of the implantable material such as thickness, density, weave pattern, knit pattern, or fenestration pattern. Accordingly, elasticity of a leaf of an implant can be adjusted or controlled by selecting specific raw materials for use in preparing an implant material of a leaf, or by selecting structural features of the leaf such as thickness, weave pattern, knit pattern, fenestration pattern, density, etc., or two or more of these in combination. According to certain embodiments of implants, a vaginal leaf (preferably both vaginal leafs) of an implant can exhibit an elasticity that is comparable to typical or average visceral mechanics, specifically elasticity, of vaginal tissue. A sacral leaf may exhibit comparatively less elasticity, e.g., be less elastic, when compared to the elasticity of a vaginal leaf.

Implant material density is a physical property of an implant material or a leaf or layer of an implant. The density of one implant layer or leaf can be the same or different from the density of a different layer or leaf of the same implant. According to specific embodiments of implants, a vaginal leaf (preferably both vaginal leafs) of an implant can exhibit a density that is less than a density of a sacral leaf. The density of the sacral leaf may be greater than the density of the vaginal leaf (preferably both vaginal leafs), e.g., may be at least 140 percent of the density of the vaginal leaf, such as from 140 to 210 percent of the density of the vaginal leaf, or from 150 to 200 percent of the vaginal leaf.

A specific density of an implant material, leaf, or layer of an implant can be any density that allows the material, leaf, or layer to function as an implant as described herein. An example of a useful range of density for a sacral leaf or a vaginal leaf is a range of density from 15 to 40 grams per square meter. According to certain embodiments, the range for a vaginal leaf can be from 15 to 25 grams per cubic centimeter, or from 20 to 25 grams per square meter. Also according to certain embodiments, the density of a sacral leaf of an implant can be greater than the density of a vaginal leaf of the implant, such as by a factor of about 1.4 to about 2; in these embodiments the sacral leaf may have a density that is from about 140 percent to about 200 percent of the density of the vaginal leaf, such as in a range from 30 to 50 grams per square meter, e.g., from 30 to 45 grams per square meter.

Useful dimensions of an implant and portions (i.e., leafs) thereof can be dependent on a variety of factors including most particularly the surgical application for which the implant is designed. Preferably, for a sacral colpopexy procedure, the dimensions of the implant and its constituent parts are at least sufficient to allow the head portion (which includes two layers with a pair of opposing and facing surfaces, each layer referred to each as a "vaginal leaf") to contact and be secured to tissue at a vaginal apex, while the end portion (referred to as the "sacral leaf") extends to tissue of a region of a sacrum, with additional size to account for the imprecision associated with the range of human anatomy sizes and for a small amount of slack.

In preferred embodiments, the maximum width of the implant and its vaginal and sacral leafs can be between about 1 and 6 centimeters; the overall length (which is the same as the length of the base, which is the combined length of the sacral leaf and the first vaginal leaf) is between about 15 and 25 cm, and the thickness is between about 0.020 inches (0.508 mm) and 0.040 inches (1.016 mm). More preferably, the overall length may be between about 18 and 24 cm, a width of a leaf can be from about 1 cm to about 4.5 cm, and the thickness is between about 0.024 inches (0.61 mm) to about 0.036 inches (0.914 mm). A preferred width of a sacral leaf can be from about 1 to 4 centimeters, e.g., from 2.2 to 3.5 centimeters. A preferred width of a vaginal leaf (e.g., two vaginal leafs) can be from about 3 to 6 centimeters, e.g., from about 4 to 5.5 centimeters.

An implant can be prepared by any desired method. Separate pieces or components such as the end portion and first and second tissue support portions can be prepared and assembled or combined by any useful method or method steps, in any suitable manner to produce a desired implant as described, optionally with two pieces or portions having different properties, e.g., different elasticity, weave or knit patterns, fenestration pattern, density, length, thickness, or width. While any method of assembling an implant can be useful, certain new methods of continuously or semi-continuously producing an intermediate web construction from which implants can be derived, and related new methods of continuously or semi-continuously producing implants, have been identified. These new continuous and semi-continuous methods have been identified as particularly useful and advantageous for producing implants that include an different portions that include one portion of a single layer and one portion of two layers, e.g., an end portion having one layer and a head portion having two layers, such as a Y-sling and similar implants.

According to continuous methods, implants can be prepared (continuously or semi-continuously) by methods that include a step of continuously forming implant material, specifically, continuously forming a first (upper) implant material and a second (lower) implant material. After or during the process of forming the first and second implant materials, the method also includes a continuous or semi-continuous process of assembling and combining the first implant material and the second implant material into an elongate and continuous segmented web construction or "ribbon" that embodies a length of multiple uncut implants. This step includes continuously producing or placing a length of the first implant material surface in contact with a length of the second implant material surface, optionally interweaving one or multiple segments or junctions of the first implant material and the second implant material at periodic locations along the length of the web construction of first and second implant materials, and alternately or additionally placing junctions in a width-wise direction at periodic locations along the length of the web construction of first and second implant materials. A continuous method also can include a step of operating on the web construction by selectively cutting the first and second implant materials of the web construction (or an inter-woven segment thereof) in a width-wise direction, at useful locations along the length of the web construction to form implants as described, such as a Y-sling.

According to exemplary methods, a first implant material (sometimes referred to as the upper implant material) and a second implant material (sometimes referred to as the lower implant material) are each continuously produced (each implant material is an open pore implant material). The phrase "continuously produced" is used in a manner consistent with the ordinary meaning of the phrase "continuous process" or the phrase "continuous manufacturing process" as those terms are used in the manufacturing arts. Accordingly, as used herein, a continuously produced implant material refers to an implant material that is or can be formed by a substantially un-interrupted, ongoing process such as a continuous weaving, knitting, or extrusion and fenestration process. The continuous process results in an integrally formed or integrally existing length (e.g., in a machine direction) of open pore implant material, the length of implant material having a width in the lateral (e.g., crossweb) direction.

Figure 3:
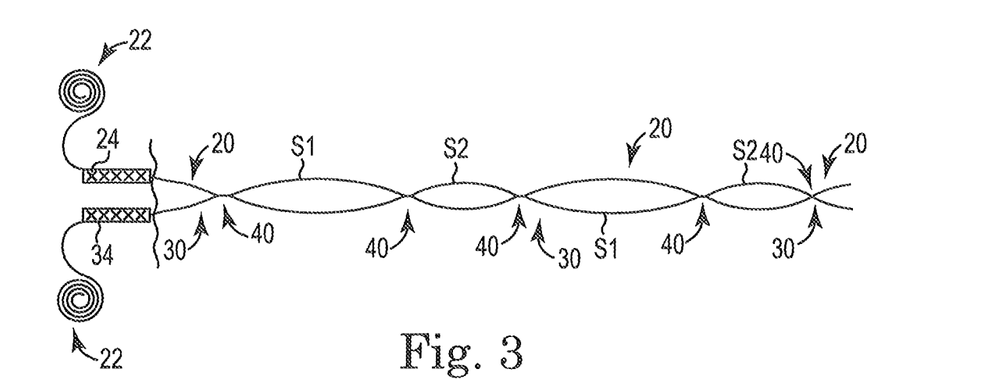
FIG. 3 shows an embodiment of apparatus and process steps for preparing a web.

FIG. 3 schematically illustrates an example of equipment and processing methods useful to produce a first (upper) open pore implant material 20 and a second (lower) open pore implant material 30. Referring to FIG. 3, supply 22 is an amount of raw material such as natural or polymeric strands, fibers, or filaments, etc., available in amount and form to supply web-producing equipment 24 and 34. Supply 22 is illustrated as having two source units, but a single source or two or more sources may also be useful. Web-forming apparatus 24 and 34 may be single (e.g., integrally operated and functioning) or separate web-forming apparatus, or single or separate components of a single web-forming apparatus; the web-forming apparatus may be any equipment useful to produce a continuous web of open pore implant material, e.g., porous implant material that may be woven, knit, or extruded (and apertured, perforated, or otherwise fenestrated). Suitable web-forming apparatus may be a loom; a knitting machine; an extruder in combination with fenestration (e.g., aperture-forming) equipment such as a perforator, cutter, knife, die-cutter, laser cutter, etc.; or another apparatus useful to continuously produce an open pore woven, knitted, or extruded-and-fenestrated implant material.

Referring still to FIG. 3, upper open pore implant material 20 continuously feeds out of apparatus 24, and lower open pore implant material 30 continuously feeds out of apparatus 34. Junctions 40 are formed regularly and intermittently along respective lengths of open pore implant materials 20 and 30 to produce segments (S1 and S2) between adjacent junctions 40. Junctions 40 can be formed in a width-wise direction across the width of upper and lower implant materials 20 and 30 to securely connect, join, or bond, implant materials 20 and 30 together. Junctions 40 may be formed by any useful method or combination of methods, such as by adhesive, thermobonding, sonic welding, RF welding, stitching (by a thread or suture separate from a thread or filament used to produce implant material 20 or 30), or interweaving. All of these methods can be performed at or near apparatus 24 and 34, with junctions formed by adhesive, thermobonding, sonic welding, RF welding, or suturing, or interweaving, optionally requiring a separate station to perform the operation downstream from the web-forming apparatus 24 and 34. Interweaving generally refers to any method of continuously knitting or weaving strands, fibers, or filaments that make up implant material 20 with strands, fibers, or filaments that make up implant material 30. As such, junctions formed by interweaving can be formed by cooperation between web-forming apparatus 24 and web-forming apparatus 34.

FIG. 3 also illustrates web construction (or "ribbon") 50, which is the construction that includes upper implant material 20 and lower implant material 30 periodically joined at junctions 40. Web construction 50 includes periodic and repeating segments S1 and S2, each formed by a length of upper open pore implant material and lower open pore implant material, joined at opposing ends by junctions 40. As illustrated, repeating segments S1 and S2 repeat in an alternating fashion: S1, S2, S1, S2, S1, S2, etc., such that web construction 50 includes tens, hundreds, or potentially thousands of alternating pairs of segments S1 and S2.

As illustrated, the length of segment S1 is greater than the length of segment S2. In these or alternate web construction embodiments, lengths of different segments (S1, S2, or otherwise) may be different or the same; periodicity may be different (e.g., additional segments S3, S4 may be included, or alternate sequencing may be used (S1, S1, S2, S2) may be possible depending on the type and construction of implant to be derived from web construction 50 by a subsequent step of cutting web construction 50 at locations to form multiple implants.

As described elsewhere herein but not specifically illustrated at FIG. 3, segments S1 and S2 may optionally exhibit different physical and mechanical properties. Each segment S1 can have its own properties, common to material 20 and 30, but different from a property of material 20 and 30 at an adjacent segment S2. For example a width, weave pattern, fenestration pattern, knit patterns, density, colors, elasticity, or other physical or mechanical property of an implant material (20 or 30) of segment S1 can be the same or different from such property of an implant material (20 or 30) of segment S2. If segment S1 is a vaginal leaf segment and segment S2 is a sacral leaf segment, the density of an implant material (20, 30) of segment S2 may be greater than the density of an implant material (20, 30) of segment S1; alternately or in combination, the elasticity of an implant material (20, 30) of segment S1 may be greater than the elasticity of an implant material (20, 30) of segment S2; alternately or in combination, the width of an implant material (20, 30) of segment S1 may be greater than the width of an implant material (20, 30) of segment S2; the specific density, elasticity, width, and other properties of an implant material (20, 30) of a vaginal leaf segment S1 or sacral leaf segment S2 can be as described elsewhere herein.

Figures 4A, 4B:
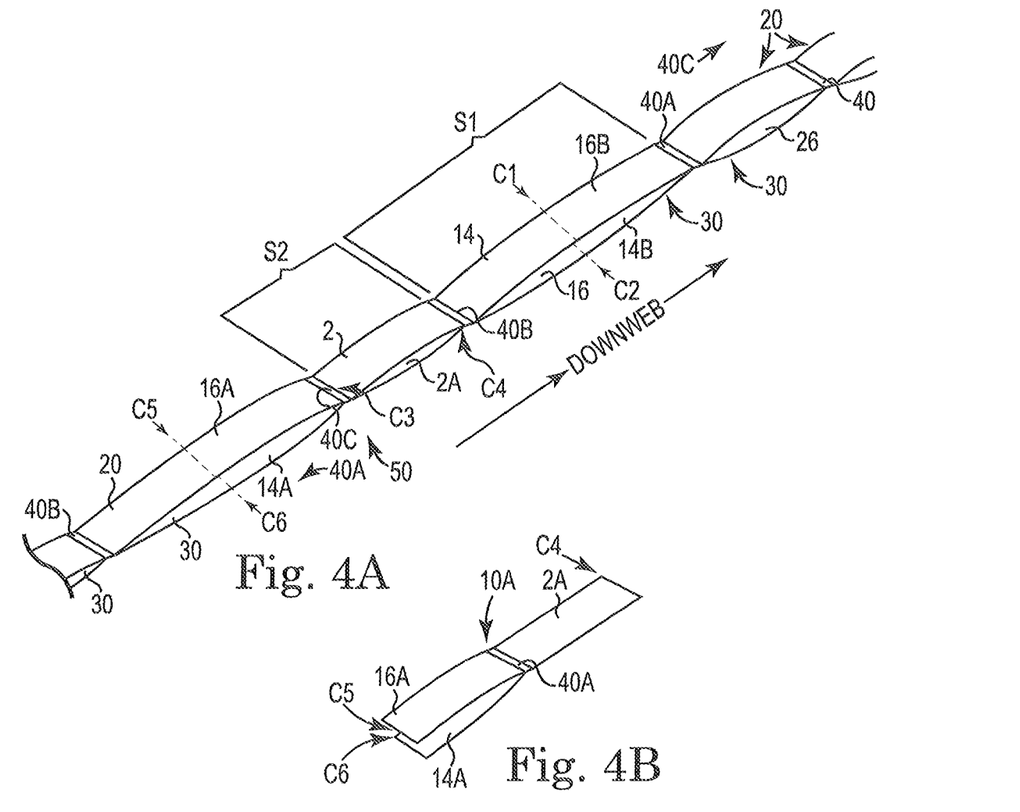
FIGS. 4A, 4B, and 4C show a web construction and implants prepared from the web construction.
Figure 4C:
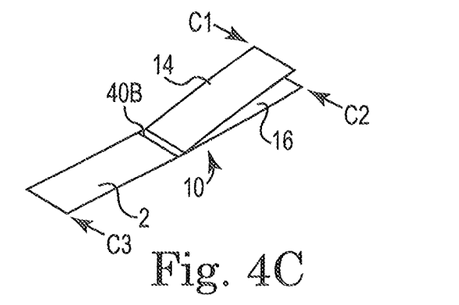

Referring now to FIGS. 4A, 4B, and 4C, web construction 50 (see FIG. 4A) is useful to produce multiple implants 10 by cutting web construction 50 at specified locations to form a multiplicity of implants, each of which exhibits substantially identical size, shape, structure, and physical and mechanical properties. As shown at FIGS. 4B and 4C a multiplicity of implants 10 and 10A (etc.) comprise a head portion 4 that includes two vaginal leafs, 14 and 16, and end portion 2. End portion 2 and vaginal leaf 14 are continuously formed and integrally connected.

Referring to FIG. 4A, web construction 50 is continuously formed of two (e.g., woven or knit) open pore implant materials: upper implant material 20 and lower implant material 30. These are joined periodically at junctions 40 (40A, 40B, and 40C, as illustrated), the junctions being formed as described elsewhere herein, such as by inter-weaving or inter-knitting strand materials used to form open pore implant material 20 and open pore implant material 30 during formation of implant materials 20 and 30. Web construction 50 can be continuously formed to produce a series of segments S1 and S2, separated by junctions 40; lengths of segments S1 and S2 are defined by junctions 40 at ends of segments S1 and S2, with junctions 40 being formed by joining (in any manner) open pore implant materials 20 and 30 of web construction 50.

Segments S1 and S2 and junctions 40 of web construction 50 are sized and spaced to allow web construction 50 to be cut in a width-wise direction at selective length-wise locations of segments S1 and S2 in a manner to result in a plurality or a multiplicity of implants 10 being produced; optionally and preferably one or more mechanical property or physical property of different portions (leafs) of each implant 10 can be different.

As illustrated at FIG. 4A, segment S1 is of a length that allows segment S1 to be cut at a midpoint location between junction 40A and 40B to form vaginal leafs 14 and 16 of implant 10 (at FIG. 4C). Width-wise cuts C1 and C2 of upper implant material 20 of segment S1, and lower implant material 30 of segment S1, result in vaginal leafs 14 and 16. Segment S1 is a vaginal leaf segment, and has a length between junctions 40A and 40B equal to a combined length of two vaginal leafs, and a width of a single vaginal leaf. (Cuts C1 and C2 simultaneously create vaginal leafs 14B and 16B of a downweb adjacent implant.) Upper implant material 20 is also cut in a width-wise direction at cut C3, adjacent to and excluding junction 40C; lower web material 30 is cut in a width-wise direction at cut C4, adjacent to (in an up-web direction) and excluding junction 40B. Segment S2 is a sacral leaf segment and has a length between junctions 40B and 40C of approximately a single sacral leaf, when upper implant material 20 is cut at C3 to exclude junction 40C, and at C4 to exclude junction 40B.

FIG. 4C shows implant 10 prepared by cutting web construction 50 at cuts C1, C2, C3, and C4. FIG. 4B shows implant 10A prepared by cutting web construction 50 at cuts C4, C3, C5, and C6. As is apparent from these figures, web construction 50, being of a length to include many (e.g., tens, hundreds, or more) alternating segments S1 and S2, can be cut at locations corresponding to C1, C2, C3, and C4 (as well as C5 and C6), to produce many (e.g., tens, hundreds, or more) implants that are substantially the same in dimensions and physical and mechanical properties as implants 10 and 10A. Each implant 10 and 10A (and any others made from web construction 50) will have substantially identical physical and mechanical properties (each leaf of implant 10 will exhibit the same length, width, density, elasticity, etc., as a corresponding leaf of implant 10A and other implants produced from web construction 50). Consequently, to the extent that one implant (e.g., 10) derived from web construction 50 includes differences in physical properties between different portions (leafs) of that implant, the same differences will also be present on other implants (e.g., 10A and additional implants) derived from web construction 50 (presuming that all repeating segments S1 have identical properties and that all repeating segments S2 have identical properties). In specific, according to certain implant embodiments, each sacral leaf segment S2 of web construction 50 can have a narrower width dimension as compared to a width dimension of vaginal leaf segment S1; each implant material 20, 30 of sacral leaf segment S2 of web construction 50 can have a relatively higher density as compared to the density of implant material 20, 30 of vaginal leaf segment S1; each implant material 20, 30 of sacral leaf segment S2 of web construction 50 can have a different weave or knit or fenestration pattern compared to the weave or knit pattern of implant material 20, 30 of vaginal leaf segment S1; each implant material 20, 30 of sacral leaf segment S2 of web construction 50 can have a relatively lower elasticity as compared to the elasticity of implant material 20, 30 of vaginal leaf segment S1; etc., as desired for a particular implant for treatment of a particular tissue condition.

Figure 5:
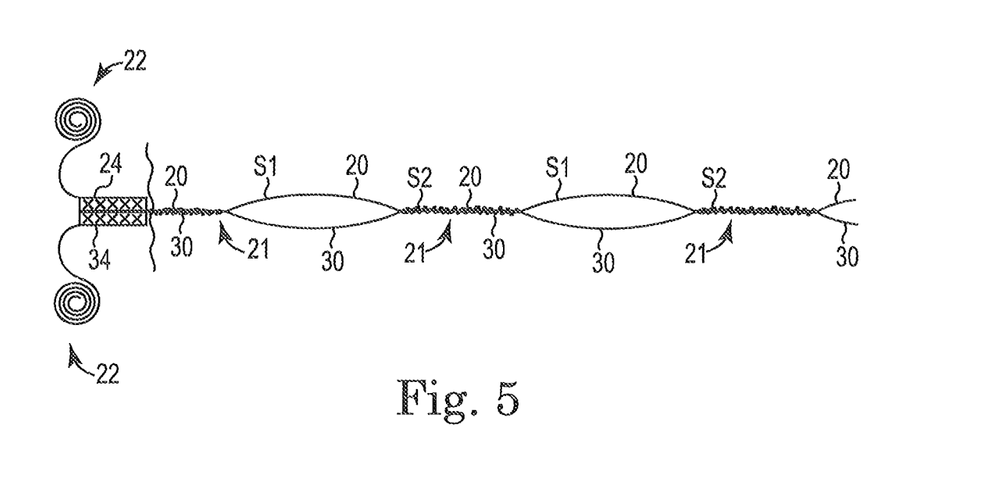
FIG. 5 shows an embodiment of apparatus and process steps for preparing a web.

FIGS. 5, 6A, 6B, and 6C illustrate alternate continuous processing methods, web constructions, and resultant implants, also within the present description. FIG. 5 schematically illustrates an example of equipment and processing methods useful to produce a first (upper) open pore implant material 20 and a second (lower) open pore implant material 30, and web construction 51. The apparatus, equipment, and web construction of FIG. 5 is similar to or the same as in FIG. 3, except that segment S2 (a sacral leaf segment) of web construction 51 of FIG. 5 is a single layer of a "combined implant material" prepared by interweaving or inter-knitting upper implant material 20 and lower implant material 30 to form a single layer of combined implant material 21.

Supply 22, web-forming apparatus 24 and 34, and upper implant material 20 and lower implant material 30 may be similar to or the same as those described in FIG. 3. In a continuous process, upper open pore implant material 20 continuously feeds out of apparatus 24, and lower open pore implant material 30 continuously feeds out of apparatus 34. Intermittently, and based on a regular and repeating sequence, interwoven (e.g., inter-knitted or inter-twined) segments S2 of a single layer of combined implant material are formed by interweaving (inter-knitting or inter-twining) respective lengths of open pore implant materials 20 and 30 as these materials are formed, to produce combined implant material 21. Interweaving generally refers to any method of continuously knitting or weaving strands, fibers, or filaments that make up implant material 20 with strands, fibers, or filaments that make up implant material 30.

Web construction (or "ribbon") 51 includes upper implant material 20 and lower implant material 30 periodically inter-woven to form combined implant material 21. Web construction 51 includes periodic and repeating segments S1 and S2, each formed by a length of upper open pore implant material and lower open pore implant material, optionally inter-woven. As illustrated, repeating segments S1 and S2 repeat in an alternating fashion: S1, S2, S1, S2, S1, S2, etc., such that web construction 50 includes tens, hundreds, or potentially thousands of alternating pairs of segments S1 and S2.

The length of segment S1 can be greater than, approximately equal to, or less than the length of segment S2. In these or alternate web construction embodiments, lengths of different segments (S1, S2, or otherwise) may be different or the same; periodicity may be different (e.g., additional segments S3, S4 may be included, or alternate sequencing may be used (S1, S1, S2, S2) may be possible depending on the type and construction of implant to be derived from web construction 51 by a subsequent step of cutting web construction 51 at locations to form multiple implants.

Segments S1 and S2 (as with those of FIG. 3) may optionally exhibit different physical and mechanical properties. Each segment S1 can have its own properties, common to material 20 and 30, but different from a property of combined implant material 21 at an adjacent segment S2. For example a width, weave pattern, fenestration pattern, knit patterns, density, colors, elasticity, or other physical or mechanical property of an implant material (20 or 30) of segment S1 can be the same or different from such property of combined implant material 21 of segment S2. If segment S1 is a vaginal leaf segment and segment S2 is a sacral leaf segment, the density of a combined implant material 21 of segment S2 may be greater than the density of an implant material (20, 30) of segment S1; alternately or in combination, the elasticity of an implant material (20, 30) of segment S1 may be greater than the elasticity of a combined implant material 21 of segment S2; alternately or in combination, the width of a combined implant material 21 of segment S2 may be less than the width of an implant material (20, 30) of segment S1; the specific density, elasticity, width, and other properties of an implant material (20, 30) of a vaginal leaf segment S1 or of combined implant material 21 of sacral leaf segment S2 can be as described elsewhere herein.

Figures 6A, 6B:
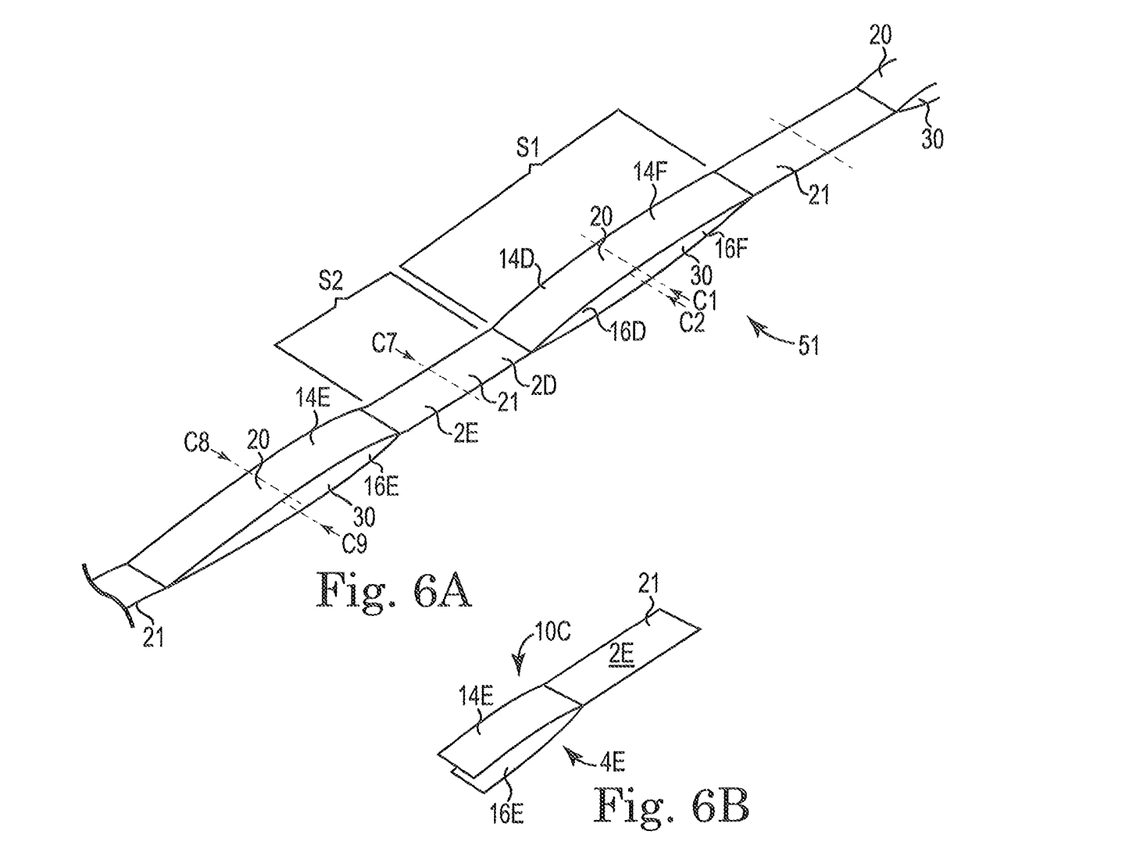
FIGS. 6A, 6B, and 6C show a web construction and implants prepared from the web construction.
Figure 6C:
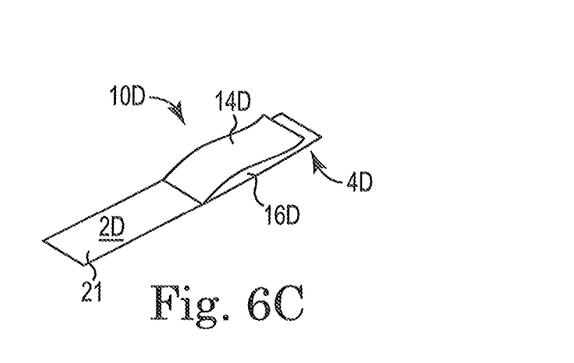

Referring now to FIGS. 6A, 6B, and 6C, web construction 51 (see FIG. 6A) is useful to produce multiple implants 10C, 10D by cutting web construction 51 at specified locations to form a multiplicity of implants, each of which exhibits substantially identical size, shape, structure, and physical and mechanical properties. A multiplicity of implants 10C and 10D (etc.) comprise a head portion 4E, 4D that includes two vaginal leafs, 14D, 14E and 16D and 16E, and end portions 2D, 2E. These implants and features thereof are similar to those of FIGS. 4B and 4C, but that sacral leafs 2D and 2E are made of higher density implant material, i.e., combined implant material 21 made by interweaving implant material 20 and implant material 30, and may have a reduced width and reduced elasticity (e.g., reduced longitudinal elasticity).

Referring to FIG. 6A, web construction 51 is continuously formed of two (e.g., woven or knit) open pore implant materials: upper implant material 20 and lower implant material 30. These are intertwined periodically at segments S2 of combined implant material 21. The series of segments S1 and S2 is continuously formed and are sized and spaced to allow web construction 51 to be cut in a width-wise direction at selective length-wise locations of segments S1 and S2 in a manner to result in a plurality or a multiplicity of implants 10C, 10D, being produced; optionally and preferably one or more mechanical property or physical property of different portions (leafs) of each implant 10C and 10D are different.

As illustrated at FIG. 6A, segment S1 is of a length that allows segment S1 to be cut at a midpoint location to form vaginal leafs 14D and 16D of implant 10D (at FIG. 6C); width-wise cuts C1 and C2 of upper implant material 20 of segment S1, and lower implant material 30 of segment S1, result in vaginal leafs 14D and 16D. Segment S1 is a vaginal leaf segment, and has a length of two vaginal leafs, and a width of a single vaginal leaf. (Cuts C1 and C2 simultaneously create vaginal leafs 14F and 16F of a downweb adjacent implant.) Combined implant material 21 is cut in a width-wise direction at cut C7; segment S2 is a sacral leaf segment and has a length of approximately two sacral leafs; when combined implant material 21 of segment S2 is cut at C7, two sacral leafs (2D and 2E) are formed, each belonging to a different implant (10D and 10C, respectively).

FIG. 6C shows implant 10D prepared by cutting web construction 51 at cuts C1, C2, and C7. FIG. 6B shows implant 10C prepared by cutting web construction 51 at cuts C7, C8, and C9. As is apparent from these figures, web construction 51, being of a length to include many (e.g., tens, hundreds, or more) alternating segments S1 and S2, can be cut at locations corresponding to C1, C2, C3, C7, C8, and C9, to produce many (e.g., tens, hundreds, or more) implants that are substantially the same as implants 10C and 10D. Each implant 10C and 10D (and any others made from web construction 50) will have substantially identical physical and mechanical properties (each leaf of an implant 10C will exhibit the same length, width, density, elasticity, etc., as a corresponding leaf of implant 10D and other implants produced from web construction 51, assuming inter-segment consistency of segments S1, and inter-segment consistency of segments S2. Consequently, to the extent that one implant (e.g., 10C) derived from web construction 51 includes differences in physical properties between different portions (leafs) of that implant, the same differences will also be present on each other implant (e.g., 10D and additional implants) derived from web construction 51 (presuming that all repeating segments S1 have identical properties and that all repeating segments S2 have identical properties). In specific, according to certain implant embodiments, each sacral leaf segment S2 of web construction 51 can have a narrower width dimension as compared to a width dimension of vaginal leaf segment S1; the combined implant material 21 of sacral leaf segment S2 of web construction 51 can have a relatively higher density as compared to the density of implant materials 20 and 30 of vaginal leaf segment S1; combined implant material 21 of sacral leaf segment S2 of web construction 51 can have a different weave or knit or fenestration pattern compared to the weave or knit pattern of implant material 20, 30 of vaginal leaf segment S1; combined implant material 21 of sacral leaf segment S2 of web construction 51 can have a relatively lower elasticity (longitudinal) as compared to the elasticity (longitudinal) of implant materials 20 and 30 of vaginal leaf segment S1; etc., as desired for a particular implant for treatment of a particular tissue condition.

Preparing a web construction (e.g., 50, 51) to exhibit the structure and properties as described can be accomplished by known methods and know equipment. To produce different weave, fenestration, or knit patterns, or elasticities of different segments of a web construction, an apparatus can operate at different settings (e.g., bar settings). To produce a web construction that includes different densities of segments, an apparatus can also operate at different settings, such as a higher speed setting to produce a lower implant material density and a lower speed setting to produce a higher implant material density.

The disclosed systems, their various components, structures, features, materials and methods may have a number of suitable configurations as shown and described in the previously-incorporated references. Various methods and tools for introducing, deploying, anchoring and manipulate device, implants, and the like as disclosed in the references incorporated herein are envisioned for use with the present invention as well. All patents, patent applications, and publications cited herein are hereby incorporated by reference in their entirety as if individually incorporated, and include those references incorporated within the identified patents, patent applications and publications.

The invention claimed is:

1. An implant, comprising:
   a base including a sacral leaf at a first end and a first vaginal leaf at a second end opposite the first end, the base being a continuous piece of open pore implant material including the sacral leaf and the first vaginal leaf as a single integrally formed material; and
   a second vaginal leaf including an attached end and a loose end, the attached end being separately attached to the base along a width of the base, wherein:
   the first vaginal leaf includes implant material having a first vaginal leaf elasticity, a first vaginal leaf width, a first vaginal leaf fenestration pattern, a first vaginal leaf density, and a marking disposed on a portion of the first vaginal leaf of a first color, the first vaginal leaf being of a second color different than the first color,
   the second vaginal leaf includes implant material having a second vaginal leaf elasticity, a second vaginal leaf width, a second vaginal leaf fenestration pattern, a second vaginal leaf density, and a marking on a portion of the second vaginal leaf of the second color, the second vaginal leaf being of the first color,
   the sacral leaf includes implant material having a sacral leaf elasticity, a sacral leaf width, a sacral leaf fenestration pattern, and a sacral leaf density, and wherein one or more of the following conditions is met:
   the sacral leaf elasticity is different from the first vaginal leaf elasticity,
   the sacral leaf elasticity is different from the second vaginal leaf elasticity,
   the sacral leaf width is different from the first vaginal leaf width,
   the sacral leaf width is different from the second vaginal leaf width,
   the sacral leaf density is different from the first vaginal leaf density,
   the sacral leaf density is different from the second vaginal leaf density,
   the sacral leaf fenestration pattern is different from the first vaginal leaf fenestration pattern, or
   the sacral leaf fenestration pattern is different from the second vaginal leaf fenestration pattern.

2. The implant according to claim 1, wherein the sacral leaf elasticity is less than the first vaginal leaf elasticity and the second vaginal leaf elasticity.

3. The implant according to claim 1, wherein the sacral leaf fenestration pattern is different from the first vaginal leaf fenestration pattern.

4. The implant according to claim 3, wherein the second vaginal leaf fenestration pattern is the same as the first vaginal leaf fenestration pattern.

5. The implant according to claim 1, wherein the attached end is attached at the base by an attachment selected from the group consisting of: interweaving, a suture, thermal-bonding, adhesive, and combinations thereof.

6. The implant according to claim 1, wherein the sacral leaf density is in a range from 30 to 50 grams per square meter and is from 140 percent to 200 percent of the first vaginal leaf density or the second vaginal leaf density.

7. The implant according to claim 1, wherein
the sacral leaf width is in a range from 1 to 4 centimeters,
the first vaginal leaf width and the second vaginal leaf width are in a range from 3 to 6 centimeters, and
the sacral leaf width is less than the first vaginal leaf width and is less than the second vaginal leaf width.

8. The implant according to claim 1, wherein the marking of the first vaginal leaf is a stripe.

9. The implant according to claim 1, wherein the marking of the second vaginal leaf is a stripe.

* * * * *